(12) United States Patent
Kiryukhin et al.

(10) Patent No.: US 8,703,446 B2
(45) Date of Patent: Apr. 22, 2014

(54) METHOD FOR PRODUCING AN L-AMINO ACID USING A BACTERIUM OF THE ENTEROBACTERIACEAE FAMILY

(71) Applicant: Ajinomoto Co., Inc., Tokyo (JP)

(72) Inventors: Mikhail Yurievich Kiryukhin, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/735,267

(22) Filed: Jan. 7, 2013

(65) Prior Publication Data

US 2013/0109063 A1    May 2, 2013

Related U.S. Application Data

(63) Continuation of application No. PCT/JP2011/066787, filed on Jul. 15, 2011.

(30) Foreign Application Priority Data

Jul. 21, 2010   (RU) ................................ 2010130307

(51) Int. Cl.
| C12P 13/04 | (2006.01) |
| C12P 13/22 | (2006.01) |
| C12P 13/08 | (2006.01) |
| C12P 13/12 | (2006.01) |
| C12P 13/06 | (2006.01) |
| C12P 13/24 | (2006.01) |
| C12P 13/20 | (2006.01) |
| C12P 13/14 | (2006.01) |
| C12P 13/10 | (2006.01) |

(52) U.S. Cl.
USPC ........... 435/106; 435/108; 435/115; 435/113; 435/116; 435/107; 435/109; 435/110; 435/114

(58) Field of Classification Search
None
See application file for complete search history.

(56) References Cited

U.S. PATENT DOCUMENTS

| 4,278,765 A | 7/1981 | Debabov et al. |
| 4,346,170 A | 8/1982 | Sano et al. |
| 5,661,012 A | 8/1997 | Sano et al. |
| 6,040,160 A | 3/2000 | Kojima et al. |
| 7,531,332 B2 | 5/2009 | Livshits et al. |
| 7,618,803 B2 | 11/2009 | Tabolina et al. |
| 7,618,804 B2 | 11/2009 | Tabolina et al. |
| 7,794,988 B2 | 9/2010 | Filippov et al. |
| 7,803,584 B2 | 9/2010 | Rybak et al. |
| 7,855,060 B2 | 12/2010 | Filippov et al. |
| 7,888,077 B2 | 2/2011 | Filippov et al. |
| 7,915,018 B2 | 3/2011 | Rybak et al. |
| 7,919,283 B2 | 4/2011 | Filippov et al. |
| 8,003,367 B2 | 8/2011 | Marchenko et al. |
| 8,003,368 B2 | 8/2011 | Marchenko et al. |
| 8,088,606 B2 | 1/2012 | Rybak et al. |
| 8,114,639 B2 | 2/2012 | Filippov et al. |
| 8,227,214 B2 | 7/2012 | Rybak et al. |
| 2002/0034793 A1 | 3/2002 | Gusyatiner et al. |
| 2003/0049803 A1* | 3/2003 | Rieping et al. ................ 435/106 |
| 2009/0137011 A1 | 5/2009 | Filippov et al. |
| 2010/0143983 A1 | 6/2010 | Kiryukhin et al. |
| 2011/0143403 A1 | 6/2011 | Rybak et al. |
| 2012/0219996 A1 | 8/2012 | Rybak et al. |
| 2012/0237986 A1 | 9/2012 | Ziyatdinov et al. |

FOREIGN PATENT DOCUMENTS

| EP | 0864654 A1 * | 9/1998 |
| EP | 1170358 | 1/2002 |
| WO | WO2012/011596 | 1/2012 |

OTHER PUBLICATIONS

Lee et al., Nucleic Acids Res. vol. 36, e102, 2008, 10 pages.*
Table 4 of Supplementary Data to Nucleic Acids Res. vol. 36, e102, 2008, 5 pages.*
EMBL Accession U000096, Sep. 2011, 12 pages.*
International Preliminary Report on Patentability for PCT Patent App. No. PCT/JP2011/066787 (Jan. 31, 2013).
Domka, J., et al., "YliH (BssR) and YceP (BssS) Regulate *Escherichia coli* K-12 Biofilm Formation by Influencing Cell Signaling," Appl. Environmen. Microbiol. 2006;72(4):2449-2459.
Office Action issued in Russian Patent App. No. 2010130307 (Feb. 7, 2013) with partial English translation thereof.
International Search Report for PCT Patent App. No. PCT/JP2011/066787 (Oct. 14, 2011).
Ren, D., et al., "Gene expression in *Escherichia coli* biofilms," Appl. Microbiol. Biotechnol. 2004;64:515-524.

* cited by examiner

*Primary Examiner* — David J Steadman
(74) *Attorney, Agent, or Firm* — Shelly Guest Cermak; Cermak Nakajima LLP

(57) ABSTRACT

The present invention provides a method for producing L-amino acid using a bacterium of the Enterobacteriaceae family, particularly a bacterium belonging to the genus *Escherichia* or *Pantoea*, which has been modified to enhance the expression of the bssR gene, which encodes a regulator of biofilm through signal secretion.

5 Claims, No Drawings

METHOD FOR PRODUCING AN L-AMINO ACID USING A BACTERIUM OF THE ENTEROBACTERIACEAE FAMILY

This application is a Continuation of, and claims priority under 35 U.S.C. §120 to, International Application No. PCT/JP2011/066787, filed Jul. 15, 2011, and claims priority therethrough under 35 U.S.C. §119 to Russian Patent Application No. 2010130307, filed Jul. 21, 2010, the entireties of which are incorporated by reference herein. Also, the Sequence Listing filed electronically herewith is hereby incorporated by reference (File name: 2013-01-07T_US-435_Seq_List; File size: 5 KB; Date recorded: Jan. 7, 2013).

FIELD OF THE INVENTION

The present invention relates to the microbiological industry, and specifically to a method for producing an L-amino acid using a bacterium of the Enterobacteriaceae family which has been modified to enhance the expression of the bssR gene. This gene encodes a regulator of biofilm through signal secretion.

BRIEF DESCRIPTION OF THE RELATED ART

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including by transforming microorganisms with recombinant DNA (U.S. Pat. No. 4,278,765). Other techniques for enhancing production yields include increasing the activities of enzymes involved in amino acid biosynthesis and/or desensitizing the target enzymes to feedback inhibition caused by the resulting L-amino acid (U.S. Pat. Nos. 4,346,170, 5,661,012 and 6,040,160).

The yliH and yceP genes are induced during the formation of *Escherichia coli* biofilms (Ren, D., et al., Appl. Microbiol. Biotechnol. (2004) 64: 515-524). It was shown that deletion of yceP (b1060) and yliH (b0836) increases biofilm formation in continuous-flow chambers with minimal glucose medium by increasing biofilm mass, surface coverage, and mean thickness. To determine the genetic basis of this increase in biofilm formation, differential gene expression profiles in biofilms were examined for both mutants, relative to the wild-type strain, in rich medium with glucose, and it was found that 372 to 882 genes were consistently induced and that 76 to 337 were consistently repressed. The increase in biofilm formation was related to differential expression of genes related to the stress response (8 to 64 genes) for both mutants. More importantly, 42 to 130 genes were related to autoinducer-2 cell signaling, and were also differentially expressed. These genes also were related to indole signaling, since 17 to 26 indole-related genes were differentially expressed. Increased biofilm formation in the yliH and yceP mutants in LB supplemented with 0.2% glucose (LB glu) occurs through a reduction in extracellular and intracellular indole concentrations in both mutants (50- to 140-fold), and the addition of indole to the culture restored the wild-type biofilm formation phenotype; hence, indole represses biofilms. Both mutants regulate biofilm formation through quorum sensing, since deletion of either yliH or yceP increased extracellular autoinducer-2 concentrations 50-fold when grown in complex medium (most notably in the stationary phase). Both proteins are involved in motility regulation, since the YliH (127 amino acids) and YceP (84 amino acids) proteins repress motility two to seven-fold in LB. New names for these two loci were proposed: bssR for yliH and bssS for yceP, based on the phrase "regulator of biofilm through signal secretion." (Domka J., et. al., Appl. Environ. Microbiol.; 72(4):2449-59 (2006)).

But currently, there have been no reports of enhancing expression of the bssR gene for the purpose of producing L-amino acids.

SUMMARY OF THE INVENTION

Aspects of the present invention include enhancing the productivity of strains which are able to produce L-amino acids and providing a method for producing an L-amino acid using these strains.

The above aspects were achieved by finding that enhancing expression of the bssR gene can enhance production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-citrulline, L-ornithine, L-phenylalanine, L-tyrosine, and L-tryptophan.

The present invention provides a bacterium of the Enterobacteriaceae family having an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-citrulline, L-ornithine, L-phenylalanine, L-tyrosine, and L-tryptophan.

It is an aspect of the present invention to provide an L-amino acid-producing bacterium of the Enterobacteriaceae family, wherein said bacterium has been modified to enhance the expression of the bssR gene.

It is a further aspect of the present invention to provide the bacterium as described above, wherein said expression is enhanced by modifying an expression control sequence of the bssR gene.

It is a further aspect of the present invention to provide the bacterium as described above, wherein said bacterium belongs to genus *Escherichia*.

It is a further aspect of the present invention to provide the bacterium as described above, wherein said bacterium is *Escherichia coli*.

It is a further aspect of the present invention to provide the bacterium as described above, wherein said bacterium belongs to genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-citrulline, and L-ornithine.

It is a further aspect of the present invention to provide the bacterium as described above, wherein said L-amino acid is L-arginine.

It is a further aspect of the present invention to provide a method for producing an L-amino acid comprising cultivating the bacterium as described above in a culture medium, and collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-citrulline, and L-ornithine.

It is a further aspect of the present invention to provide the method as described above, wherein said L-amino acid is L-arginine.

DESCRIPTION OF THE PREFERRED EMBODIMENTS

Bacterium

The bacterium in accordance with the presently disclosed subject matter is an L-amino acid-producing bacterium of the Enterobacteriaceae family, wherein the bacterium has been modified to enhance expression of the bssR gene.

The phrase "L-amino acid-producing bacterium" can mean a bacterium which has an ability to produce and excrete an L-amino acid into a medium, when the bacterium is cultured in the medium.

The term "L-amino acid-producing bacterium" also can mean a bacterium which is able to produce and cause accumulation of an L-amino acid in a culture medium in an amount larger than a wild-type or parental strain of a bacterium of the Enterobacteriaceae family, for example *E. coli*, such as *E. coli* K-12, and can mean that the microorganism is able to cause accumulation in a medium of an amount not less than 0.5 g/L, in another example, not less than 1.0 g/L, of the target L-amino acid. The bacterium can produce one kind of L-amino acid or mixture of two or more kinds of L-amino acids.

The term "L-amino acid" includes, for example, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes, for example, L-phenylalanine, L-tyrosine, and L-tryptophan. The term "non-aromatic L-amino acid" includes, for example, L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particular examples.

The Enterobacteriaceae family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella*, *Yersinia*, etc. Specifically, those classified into the family Enterobacteriaceae according to the taxonomy used by the NCBI (National Center for Biotechnology Information) database (world wide web at ncbi.nlm.nih.gov/Taxonomy/Browser/wwwtax.cgi?id=543) can be used. A bacterium belonging to the genus *Escherichia* or *Pantoea* are particular examples.

The phrase "a bacterium belonging to the genus *Escherichia*" can mean that the bacterium is classified into the genus *Escherichia* according to the classification known to a person skilled in the art of microbiology. Examples of a bacterium belonging to the genus *Escherichia* include, but are not limited to, *Escherichia coli* (*E. coli*).

The bacterium belonging to the genus *Escherichia* is not particularly limited, however, for example, bacteria described by Neidhardt, F. C. et al. (*Escherichia coli* and *Salmonella typhimurium*, American Society for Microbiology, Washington D.C., 1208, Table 1) can be used.

The phrase "a bacterium belonging to the genus *Pantoea*" can mean that the bacterium is classified as the genus *Pantoea* according to the classification known to a person skilled in the art of microbiology. Some species of *Enterobacter agglomerans* have been recently re-classified into *Pantoea agglomerans*, *Pantoea ananatis*, *Pantoea stewartii* or the like, based on the nucleotide sequence analysis of 16S rRNA, etc. (Int. J. Syst. Bacteriol., 43, 162-173 (1993)).

The phrase "the bacterium has been modified to enhance the expression of the gene" can mean that the expression of the gene is higher than that of a non-modified strain, for example, a wild-type strain. Examples of such modification include increasing the copy number of expressed gene per cell, increasing the transcription level of the gene, increasing translation level of the mRNA transcribed from the gene, and so forth. The quantity of the copy number of an expressed gene is measured, for example, by restricting the chromosomal DNA followed by Southern blotting using a probe based on the gene sequence, fluorescence in situ hybridization (FISH), and the like. The level of gene transcription can be measured by various known methods including Northern blotting, quantitative RT-PCR, and the like. The level of translation of the mRNA, or the amount of the gene product can be measured by various known methods including Western blotting using antibodies. Western blotting analysis also reflects transcription level along with translation level. Furthermore, wild-type strains that can act as a control include, for example, *Escherichia coli* K-12 or *Pantoea ananatis* Ferm BP-6614.

The bssR gene (synonyms: yliH, b0836) encodes the regulator of biofilm formation BssR. The bssR gene (nucleotides from 877,471 to 877,854; GenBank accession no. NC_000913.2; gi: 49175990) is located between the rimO gene, oriented in opposite direction, and the yliI gene on the chromosome of *E. coli* K-12. The nucleotide sequence of the bssR gene and the amino acid sequence of BssR protein encoded by the bssR gene are shown in SEQ ID NO: 1 and SEQ ID NO: 2, respectively.

Since there may be some differences in DNA sequences between the genera or strains of the Enterobacteriaceae family, the bssR gene to be modified to enhance its expression is not limited to the gene shown in SEQ ID No:1, but can include genes homologous to SEQ ID No:1. Therefore, the protein variant encoded by the bssR gene can have a homology of not less than 80%, in another example not less than 90%, in another example not less than 95%, in another example not less than 98%, and in another example not less than 99%, with respect to the entire amino acid sequence shown in SEQ ID NO. 2, as long as the protein variant has the activity of the BssR protein. The term "homology" can mean "identity".

The phrase "protein variant" can mean proteins which have changes in their sequences, whether they are deletions, insertions, additions, or substitutions of one or several amino acids. The number of changes in the variant proteins depends on the position in the three dimensional structure of the protein or the type of amino acid residues. It can be 1 to 30, in another example 1 to 15, and in another example 1 to 5 in SEQ ID NO: 2. These changes in the variants can occur in regions of the protein which are not critical for the three dimensional structure of the protein. This is because some amino acids have high homology to one another so the three dimensional structure is not affected by such a change.

Homology between two amino acid sequences can be determined using well-known methods, for example, the computer program BLAST 2.0, which calculates three parameters: score, identity and similarity.

The substitution, deletion, insertion or addition of one or several amino acid residues should be conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Moreover, the bssR gene can be a variant which hybridizes under stringent conditions with the nucleotide sequence shown in SEQ ID NO: 1, or a probe which can be prepared from the nucleotide sequence, provided that it encodes a functional BssR protein. "Stringent conditions" include those under which a specific hybrid, for example, a hybrid having homology of not less than 60%, in another example not less than 70%, in another example not less than 80%, in another example not less than 90%, in another example not less than 95%, in another example not less than 98%, and in another example not less than 99%, is formed and a non-specific hybrid, for example, a hybrid having homology lower than the above, is not formed. For example, stringent conditions can be exemplified by washing one time or more, or in another example, two or three times, at a salt concentration of 1×SSC, 0.1% SDS, or in another example, 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. The washing step can be performed 2 to 3 times. The length of the probe can be suitably selected depending on the hybridization conditions, and is usually 100 bp to 1 kbp.

Methods of enhancing gene expression include increasing the gene copy number. Introducing a gene into a vector that is able to function in a bacterium of the Enterobacteriaceae family increases the copy number of the gene. Low copy vectors can be used. Examples of low-copy vectors include, but are not limited to, pSC101, pMW118, pMW119, and the like. The term "low copy vector" is used when the copy number of the vector is up to 5 copies per cell. However, high copy vectors such as pBR-derived plasmids also can be used.

Enhancement of gene expression can also be achieved by introducing multiple copies of the gene into a bacterial chromosome by, for example, homologous recombination, Mu integration, or the like. For example, one act of Mu integration allows for the introduction of up to 3 copies of the gene into a bacterial chromosome.

Increasing the copy number of a gene can also be achieved by introducing multiple copies of the gene into the chromosomal DNA of the bacterium. In order to introduce multiple copies of the gene into a bacterial chromosome, homologous recombination is carried out using multiple copies of a sequence as targets in the chromosomal DNA. Sequences having multiple copies in the chromosomal DNA include, but are not limited to repetitive DNA, or inverted repeats present at the end of a transposable element. Also, it is possible to incorporate the gene into a transposon, and allow it to be transferred to introduce multiple copies of the gene into the chromosomal DNA.

Enhancing gene expression can also be achieved by modifying an expression control sequence of the gene such as promoter, terminator and Shine-Dalgarno (SD) sequence, for example, by placing the objective gene under the control of a potent promoter. For example, the lac promoter, the trp promoter, the trc promoter, the PR, or the PL promoters of lambda phage are all known to be potent promoters. The use of a potent promoter can be combined with multiplication of gene copies. Alternatively, the effect of a promoter can be enhanced by, for example, introducing a mutation into the promoter to increase the transcription level of a gene located downstream of the promoter. Furthermore, it is known that the substitution of several nucleotides in the spacer region between ribosome binding site (RBS) and the start codon, especially the sequences immediately upstream of the start codon, can profoundly affect the mRNA translatability. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984).

Moreover, it is also possible to introduce a nucleotide substitution into the promoter region of a gene on the bacterial chromosome, which results in a stronger promoter function. The alteration of the expression control sequence can be performed, for example, in the same manner as the gene substitution using a temperature-sensitive plasmid, as disclosed in WO 00/18935 and JP 1-215280 A.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid Producing Bacteria

As a bacterium in accordance with the presently disclosed subject matter which is modified to enhance the expression of the bssR gene, bacteria which are able to produce either an aromatic or a non-aromatic L-amino acids can be used.

The bacterium in accordance with the presently disclosed subject matter can be obtained by enhancing expression of the bssR gene in a bacterium which inherently has the ability to produce L-amino acid. Alternatively, the bacterium in accordance with the presently disclosed subject matter can be obtained by imparting the ability to produce L-amino acid to a bacterium already having the enhanced expression of the bssR gene.

L-Threonine Producing Bacteria

Examples of L-threonine-producing bacteria or parent strains, which can be used to derive the L-threonine producing bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939, 307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russia, 117105 Moscow, Nagatinskaya Street 3-A) under the accession number RIA 1867. The strain was also deposited in the Russian National Collection of Industrial Microorganisms (VKPM) (GNII genetika, 1 Dorozhny proezd, 1, Moscow 117545, Russian Federation) on Apr. 7, 1987 under the accession number VKPM B-3996.

*E. coli* VKPM B-5318 (EP 0593792B) may also be used as a parent strain for deriving L-threonine-producing bacteria. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

The bacterium can be additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession no. NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession no. NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession no. NC_000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-Lysine Producing Bacteria

Examples of L-lysine producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of L-lysine-producing bacteria or parent strains, which can be used to derive L-lysine producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenase (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains, which can be used to derive L-lysine producing bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827, 698), and the malic enzyme (WO2005/010175).

L-Cysteine Producing Bacteria

Examples of L-cycleine-producing bacteria or parent strains which can be used to derive L-cysteine producing bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (W00127307A1), and the like.

L-Leucine Producing Bacteria

Examples of L-leucine-producing bacteria or parent strains which can be used to derive L-leucine producing bacteria include, but are not limited to, strains belonging to the genus *Escherichia*, such as *E. coli* strains resistant to leucine (for example, the strain 57 (VKPM B-7386, U.S. Pat. No. 6,124, 121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium can be improved by enhancing the expression of one or more genes involved in L-leucine biosynthesis. Examples include genes of the leuABCD operon, which are preferably represented by a mutant leuA gene coding for isopropylmalate synthase which is free from feedback inhibition by L-leucine (U.S. Pat. No. 6,403,342). In addition, the bacterium can be improved by enhancing the expression of one or more genes coding for proteins which excrete L-amino acid from the bacterial cell. Examples of such genes include the b2682 and b2683 genes (ygaZH genes) (EP 1239041 A2).

L-Histidine Producing Bacteria

Examples of L-histidine-producing bacteria or parent strains which can be used to derive L-histidine producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains, which can be used to derive L-histidine producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation into ATP phosphoribosyltransferase which imparts resistance to the feedback inhibition (Russian Patent Nos. 2003677 and 2119536).

Specific examples of strains having an L-histidine producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid Producing Bacteria

Examples of L-glutamic acid-producing bacteria or parent strains which can be used to derive L-glutamic acid producing bacteria include, but are not limited to, strains belonging to the genus *Escherichia*, such as *E. coli* VL334thrC+ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 which was grown on wild-type *E. coli* K12 (VKPM B-7) cells. As a result, an L-isoleucine auxotrophic strain VL334thrC+ (VKPM B-8961), which is able to produce L-glutamic acid, was obtained.

Examples of parent strains, which can be used to derive the L-glutamic acid-producing bacteria include, but are not limited to, strains which are deficient in α-ketoglutarate dehydrogenase activity, or strains in which one or more genes encoding an L-glutamic acid biosynthetic enzyme are enhanced. Examples of the genes involved in L-glutamic acid biosynthesis include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of strains which have been modified so that expression of the citrate synthetase gene and/or the phosphoenolpyruvate carboxylase gene are reduced, and/or/are deficient in α-ketoglutarate dehydrogenase activity include those disclosed in EP1078989A, EP955368A, and EP952221A.

Examples of parent strains, which can be used to derive the L-glutamic acid producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

E. coli W3110sucA::Kmr
E. coli AJ12624 (FERM BP-3853)
E. coli AJ12628 (FERM BP-3854)
E. coli AJ12949 (FERM BP-4881)

E. coli W3110sucA::Kmr is a strain obtained by disrupting the α-ketoglutarate dehydrogenase gene (hereinafter referred to as "sucA gene") of E. coli W3110. This strain is completely deficient in the α-ketoglutarate dehydrogenase.

Other examples of L-glutamic acid producing bacterium include those which belong to the genus *Escherichia* and have resistance to an aspartic acid antimetabolite. These strains can also be deficient in the α-ketoglutarate dehydrogenase activity and include, for example, E. coli AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid producing bacteria include mutant strains belonging to the genus *Pantoea* which are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in the α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine Producing Bacteria

Examples of L-phenylalanine-producing bacteria or parent strains which can be used to derive L-phenylalanine producing bacteria include, but are not limited to, strains belonging to the genus *Escherichia*, such as E. coli AJ12739 (tyrA:: Tn10, tyrR) (VKPM B-8197); E. coli HW1089 (ATCC 55371) harboring the mutant pheA34 gene (U.S. Pat. No. 5,354,672); E. coli MWEC101-b (KR8903681); E. coli NRRL B-12141, NRRL B-12145, NRRL B-12146 and NRRL B-12147 (U.S. Pat. No. 4,407,952). Also, as a parent strain, E. coli K-12 [W3110 (tyrA)/pPHAB (FERM BP-3566), E. coli K-12 [W3110 (tyrA)/pPHAD] (FERM BP-12659), E. coli K-12 [W3110 (tyrA)/pPHATerm] (FERM BP-12662) and E. coli K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan Producing Bacteria

Examples of L-tryptophan-producing bacteria or parent strains which can be used to derive the L-tryptophan producing bacteria include, but are not limited to, strains belonging to the genus *Escherichia*, such as E. coli JP4735/pMU3028 (DSM10122) and JP6015/pMU91 (DSM10123) which is deficient in the tryptophanyl-tRNA synthetase encoded by mutant trpS gene (U.S. Pat. No. 5,756,345); E. coli SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); E. coli AGX17 (pGX44) (NRRL B-12263) and AGX6(pGX50)aroP (NRRL B-12264) deficient in the enzyme tryptophanase (U.S. Pat. No. 4,371,614); E. coli AGX17/pGX50,pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent applications 2003/0148473 A1 and 2003/0157667 A1).

Examples of parent strains for deriving the L-tryptophan producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a E. coli SV164 which harbors desensitized anthranilate synthase and a transformant strain obtained by introducing into the E. coli SV164 the plasmid pGH5 (WO 94/08031), which contains a mutant serA gene encoding feedback-desensitized phosphoglycerate dehydrogenase.

Examples of parent strains for deriving the L-tryptophan producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline Producing Bacteria

Examples of L-proline-producing bacteria or parent strains which can be used to derive L-proline producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium can be improved by enhancing the expression of one or more genes involved in L-proline biosynthesis. Examples of such genes for L-proline producing bacteria which are preferred include the proB gene coding for glutamate kinase of which feedback inhibition by L-proline is desensitized (DE Patent 3127361). In addition, the bacterium can be improved by enhancing the expression of one or more genes coding for proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami winter symposium, 1983, p. 34), and the like.

L-Arginine Producing Bacteria

Examples of L-arginine-producing bacteria or parent strains which can be used to derive L-arginine producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Citrulline Producing Bacteria

Examples of L-citrulline-producing bacteria or parent strains which can be used to derive L-citrulline producing bacteria include, but are not limited to, strains belonging to the genus *Escherichia*, such as *E. coli* mutant N-acetylglutamate synthase strains 237/pMADS11, 237/pMADS12 and 237/pMADS13 (RU2215783, EP1170361B1, U.S. Pat. No. 6,790,647B2), *E. coli* strains 333 (VKPM B-8084) and 374 (VKPM B-8086), both harboring mutant feedback-resistant carbamoyl phosphate synthetase (Russian Patent RU2264459 C2), strains *E. coli*, in which α-ketoglutarate synthase activity is increased, and ferredoxin NADP+ reductase, pyruvate synthase or α-ketoglutarate dehydrogenase activities are additionally modified (EP 2133417 A1), and strain *P. ananantis* NA1sucAsdhA, in which succinate dehydrogenase and α-ketoglutarate dehydrogenase activities are decreased (US Patent Application No 2009286290), and the like.

As L-citrulline is an intermediate of L-arginine biosynthetic pathway, examples of parent strains, which can be used to derive L-citrulline-producing bacteria, include strains, in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), and carbamoyl phosphate synthetase (carAB), or combinations thereof.

Also citrulline producing bacterium can be easely obtained from any arginine producing bacterium, for example *E. coli* stain 382 (VKPM B-7926), by inactivation of argininosuccinate synthase encoded by argG gene.

The phrase "inactivation of argininosuccinate synthase" means that the bacterium has been modified in such a way that the modified bacterium contains inactive argininosuccinate synthase or it can also mean that the bacterium is unable to synthesize the argininosuccinate synthase. Inactivation of argininosuccinate synthase can be performed by inactivation of argG gene.

The phrase "inactivation of the argG gene" means that the modified gene encodes a completely non-functional protein. It is also possible that the modified DNA region is unable to naturally express the gene due to the deletion of a part of the gene or the whole gene, the shifting of the reading frame of the gene, the introduction of missense/nonsense mutation(s), or the modification of an adjacent region of the gene, including sequences controlling gene expression, such as a promoter, enhancer, attenuator, ribosome-binding site, etc.

The presence or absence of the argG gene on the chromosome of a bacterium can be detected by well-known methods, including PCR, Southern blotting, and the like. In addition, the level of gene expression can be estimated by measuring the amount of mRNA transcribed from the gene using various well-known methods, including Northern blotting, quantitative RT-PCR, and the like. The amount of the protein encoded by the argG gene can be measured by well-known methods, including SDS-PAGE followed by an immunoblotting assay (Western blotting analysis), and the like.

Expression of the argG gene can be attenuated by introducing a mutation into the gene on the chromosome so that the intracellular activity of the protein encoded by the gene is decreased as compared with an unmodified strain. Mutations which result in attenuation of expression of the gene include the replacement of one base or more to cause an amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the argG gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein with decreased activity is prepared, and the bacterium to be modified is transformed with a DNA fragment containing the mutant gene. Then, the native gene on the chromosome is replaced with the mutant gene by homologous recombination, and the resulting strain is selected. Gene replacement or disruption using homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by employing a plasmid containing a temperature-sensitive replication origin (U.S. Pat. No. 6,303, 383 or JP 05-007491A). Furthermore, site-specific mutation by gene substitution can also be incorporated using homologous recombination such as set forth above using a plasmid which is unable to replicate in the host.

Expression of the gene can also be attenuated by inserting a transposon or an IS factor into the coding region of the gene (U.S. Pat. No. 5,175,107), or by conventional methods, such as by mutagenesis with UV irradiation or nitrosoguanidine (N-methyl-N'-nitro-N-nitrosoguanidine).

L-Ornithine Producing Bacteria

L-ornithine producing bacterium can be easily obtained from any arginine producing bacterium, for example *E. coli* stain 382 (VKPM B-7926), by inactivation of ornithine carbamoyltransferase encoded by both argF and argI genes. Methods for inactivation of ornithine carbamoyltransferase are described above.

L-Valine Producing Bacteria

Examples of L-valine-producing bacteria or parent strains which can be used to derive L-valine producing bacteria include bacteria belonging to the genus *Escherichia* such as H-81 (VKPM B-8066), NRRL B-12287 and NRRL B-12288 (U.S. Pat. No. 4,391,907), VKPM B-4411 (U.S. Pat. No. 5,658,766), VKPM B-7707 (European patent application EP1016710A2), or the like.

Example of parent strains which can be used to derive L-valine producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine producing bacteria also include mutants having a mutation of aminoacyl t-RNA synthetase (U.S. Pat. No. 5,658,766). For example, *E. coli* VL1970, which has a mutation in the ileS gene encoding isoleucine tRNA synthetase, can be used. *E. coli* VL1970 was deposited in the Russian National Collection of Industrial Microorganisms (VKPM) (GNII genetika, 1 Dorozhny proezd, 1, Moscow 117545, Russian Federation) on Jun. 24, 1988 under accession number VKPM B-4411.

Furthermore, mutants requiring lipoic acid for growth and/or lacking H+-ATPase can also be used as parent strains (WO96/06926).

L-Isoleucine Producing Bacteria

Examples of L-isoleucine-producing bacteria or parent strains which can be used to derive L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

L-Methionine-Producing Bacteria

Examples of L-methionine-producing bacteria and parent strains which can be used to derive L-methionine producing bacteria include, but are not limited to, L-threonine-auxotrophic mutant strain and norleucine-resistant mutant strain (JP 2000-139471 A). Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as parent strains.

Method

Exemplary methods in accordance with the presently disclosed subject matter include producing an L-amino acid by cultivating the bacterium in accordance with the presently disclosed subject matter in a culture medium to produce and excrete the L-amino acid into the medium, and collecting the L-amino acid from the medium.

The cultivation, collection, and purification of an L-amino acid from the medium and the like may be performed in a manner similar to conventional fermentation methods wherein an amino acid is produced using a bacterium.

The medium chosen for the culture can be either a synthetic or natural medium, so long as the medium includes a carbon source and a nitrogen source and minerals and, if necessary, appropriate amounts of nutrients which the chosen bacterium requires for growth. The carbon source may include various carbohydrates such as glucose and sucrose, and various organic acids. Depending on the mode of assimilation of the used microorganism, alcohol, including ethanol and glycerol, can be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as by shaking and/or stirring with aeration, at a temperature of 20 to 40° C., or in another example, 30 to 38° C. The pH of the culture is usually between 5 and 9, or in another example, between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting examples.

Example 1

Construction of the *E. coli* Strain MG1655::Pl-tacbssR

The *E. coli* strain MG1655::Pl-tacbssR was obtained by substitution of the native promoter region of bssR gene in strain MG1655 by Pl-tac promoter.

To substitute the native promoter region of the bssR gene, the DNA fragment carrying a Pl-tac promoter and chloramphenicol resistance marker (CmR) encoded by the cat gene was integrated into the chromosome of the *E. coli* MG1655 in the place of the native promoter region by the method described by Datsenko K. A. and Wanner B. L. (Proc. Natl. Acad. Sci. USA, 2000, 97, 6640-6645), which is also called "Red-mediated integration" and/or "Red-driven integration".

The fragment of PL-tac promoter conjunct with cat gene was obtained by PCR using chromosomal DNA of the *E. coli* strain MG1655PL-tacxylE (WO2006/043730) as a template. The nucleotide sequence of the PL-tac promoter is presented in the Sequence Listing (SEQ ID NO: 3). Primers P1 (SEQ ID NO: 4) and P2 (SEQ ID NO: 5) were used for PCR amplification. Primer P1 contains 36 nucleotides complementary to the region located 166 bp upstream of the start codon of the bssR gene introduced into the primer for further integration into the bacterial chromosome and primer P2 contains 36 nucleotides identical to 5'-sequence of bssR gene.

PCR was provided using the "Gene Amp PCR System 2700" amplificatory (Applied Biosystems). The reaction mixture (total volume—50 µl) consisted of 5 µl of 10×PCR-buffer with 15 mM MgCl2 ("Fermentas", Lithuania), 200 µM each of dNTP, 25 µmol each of the exploited primers and 1 U of Taq-polymerase ("Fermentas", Lithuania). Approximately 20 ng of the *E. coli* MG1655PL-tacxylE genomic DNA was added in the reaction mixtures as a template for PCR.

The temperature profile was the following: initial DNA denaturation for 5 min at 95° C., followed by 35 cycles of denaturation at 95° C. for 30 sec, annealing at 54° C. for 30 sec, elongation at 72° C. for 1.5 min and the final elongation for 5 min at 72° C. Then, the amplified DNA fragment was purified by agarose gel-electrophoresis, extracted using "GenElute Spin Columns" ("Sigma", USA) and precipitated by ethanol. The obtained DNA fragment was used for electroporation and Red-mediated integration into the bacterial chromosome of the *E. coli* MG1655/pKD46. The pKD46 plasmid (Datsenko, K. A. and Wanner, B. L., Proc. Natl. Acad. Sci. USA, 2000, 97:12:6640-45) contains a temperature-sensitive replication origin, and includes a 2,154 nucleotide DNA fragment of phage λ (nucleotide positions 31088 to 33241, GenBank accession no. J02459), as well as the genes of the λ Red homologous recombination system (γ, β, exo genes), which are under the control of the arabinose-inducible ParaB promoter. The pKD46 plasmid is necessary for integration of the PCR product into the chromosome of the MG1655 strain. The strain MG1655 can be obtained from American Type Culture Collection. (P.O. Box 1549 Manassas, Va. 20108, U.S.A.).

MG1655/pKD46 cells were grown overnight at 30° C. in the liquid LB-medium with the addition of ampicillin (100 µg/ml), then diluted 1:100 with the SOB-medium (Yeast extract, 5 g/l; NaCl, 0.5 g/l; Tryptone, 20 g/l; KCl, 2.5 mM; MgCl2, 10 mM) with the addition of ampicillin (100 µg/ml) and L-arabinose (10 mM) (arabinose is used for inducing the plasmid encoding genes of the Red system) and grown at 30° C. to reach the optical density of the bacterial culture OD600=0.4-0.7. Grown cells from 10 ml of the bacterial culture were washed 3 times with the ice-cold de-ionized water, followed by suspending in 100 µl of the water. 10 µl of DNA fragment (100 ng) dissolved in the de-ionized water was added to the cell suspension. The electroporation was performed by "Bio-Rad" electroporator (USA) (No. 165-2098, version 2-89) according to the manufacturer's instructions. Shocked cells were added to 1-ml of SOC medium (Sambrook et al, "Molecular Cloning A Laboratory Manual, Second Edition", Cold Spring Harbor Laboratory Press (1989)), incubated 2 hours at 37° C., and then were spread onto L-agar containing 25 µg/ml of chloramphenicol. Colonies which grew within 24 hours were tested for the presence of CmR marker, instead of the native promoter region of the bssR gene by PCR using primers P3 (SEQ ID NO: 6) and P4 (SEQ ID NO: 7). For this purpose, a freshly isolated colony was suspended in 20 µl water and then 1 µl of the obtained suspension was used for PCR. The following temperature profile was used: initial DNA denaturation for 10 min at 95° C.; then 30 cycles of denaturation at 95° C. for 30 sec, annealing at 55° C. for 30 sec and elongation at 72° C. for 1 min; the final elongation for 7 min at 72° C. A few CmR colonies tested contained the desired ~2000 bp DNA fragment, confirming the presence of Pl-tac promoter and CmR marker DNA instead of 255 bp native promoter region of bssR gene. One of these strains was cured from the thermosensitive plasmid pKD46 by culturing at 37° C. and the resulting strain was named as *E. coli* MG1655PL-tacbssR.

Example 2

Production of L-Arginine by *E. coli* 382 Pl-tacbssR

To test the effect of enhanced expression of the bssR gene which is under the control of PL-tac promoter on arginine production, DNA fragments from the chromosome of the above-described *E. coli* MG1655PL-tacbssR were transferred to the arginine-producing *E. coli* strain 382 by P1 transduction (Miller, J. H. (1972) Experiments in Molecular Genetics, Cold Spring Harbor Lab. Press, Plainview, N.Y.). The strain 382 was deposited in the Russian National Collection of Industrial Microorganisms (VKPM) (GNII genetika, 1 Dorozhny proezd, 1, Moscow 117545, Russian Federation) on Apr. 10, 2000 under accession number VKPM B-7926.

Both strains, 382 and 382 Pl-tacbssR, were separately cultivated with shaking at 37° C. for 18 hours in 3 ml of nutrient broth, and 0.3 ml of the cultures were inoculated into 2 ml of a fermentation medium in 20×200-mm test tubes on a rotary shaker at 37° C. for 48 hours.

After the cultivation, the amount of L-arginine which had accumulated in the medium was determined by paper chromatography using the following mobile phase:butanol:acetic acid:water=4:1:1 (v/v). A solution of ninhydrin (2%) in acetone was used as a visualizing reagent. A spot containing L-arginine was cut out, the L-arginine was eluted with 0.5% water solution of CdCl2, and the amount of L-arginine was estimated spectrophotometrically at 540 nm.

The composition of the fermentation medium (g/l) is as follows:

| | |
|---|---|
| Glucose | 48.0 |
| (NH$_4$)$_2$SO$_4$ | 35.0 |
| KH$_2$PO$_4$ | 2.0 |
| MgSO$_4$·7H$_2$O | 1.0 |
| Thiamine HCl | 0.0002 |
| Yeast extract | 1.0 |
| L-isoleucine | 0.1 |
| CaCO$_3$ | 5.0 |

Glucose and magnesium sulfate are sterilized separately. CaCO$_3$ is dry-heat sterilized at 180 C for 2 hours. The pH is adjusted to 7.0.

The results of test tube fermentations are shown in Table 1. As it can be seen from the Table 1, strain 382 Pl-tacbssR with enhanced expression of bssR gene was able to produce a higher amount of accumulation of L-arginine as compared with the parent L-arginine producing *E. coli* strain 382.

TABLE 1

| Strain | Amount of L-arginine, g/l 37° C. |
|---|---|
| 382 (control) | 6.2 ± 0.1 |
| 382 Pltac bssR | 8.1 ± 0.1 |

Example 3

Production of L-Threonine by *E. coli* Strain B-3996 Pl-tacbssR

To test the effect of enhancing expression of the bssR gene on threonine production, the DNA fragments from the chromosome of the above-described *E. coli* MG1655 Pl-tacbssR can be transferred to the threonine-producing *E. coli* strain VKPM B-3996 by P1 transduction (Miller, J. H. Experiments in Molecular Genetics, Cold Spring Harbor Lab. Press, 1972, Plainview, N.Y.) to obtain B-3996 Pl-tacbssR. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (GNII genetika, 1 Dorozhny proezd, 1, Moscow 117545, Russian Federation) under the accession number B-3996.

Both *E. coli* strains, B-3996 and B-3996 Pl-tacbssR, can be grown for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% glucose. Then, the fermentation medium can be inoculated with 0.21 ml (10%) of seed material. The fermentation can be performed in 2 ml of minimal medium for fermentation in 20×200-mm test tubes. Cells can be grown for 65 hours at 32° C. with shaking at 250 rpm.

After cultivation, the amount of L-threonine, which had accumulated in the medium, can be determined by paper chromatography using the following mobile phase: butanol-acetic acid-water=4:1:1 (v/v). A solution of ninhydrin (2%) in acetone can be used as a visualizing reagent. A spot containing L-threonine can be cut out, L-threonine can be eluted with 0.5% water solution of CdCl2, and the amount of L-threonine can be estimated spectrophotometrically at 540 nm.

The composition of the fermentation medium (g/l) is as follows:

| | |
|---|---|
| Glucose | 80.0 |
| (NH$_4$)$_2$SO$_4$ | 22.0 |
| NaCl | 0.8 |
| KH$_2$PO$_4$ | 2.0 |
| MgSO$_4$·7H$_2$O | 0.8 |
| FeSO$_4$·7H$_2$O | 0.02 |
| MnSO$_4$·5H$_2$O | 0.02 |
| Thiamine HCl | 0.0002 |
| Yeast extract | 1.0 |
| CaCO$_3$ | 30.0 |

Glucose and magnesium sulfate are sterilized separately. CaCO$_3$ is sterilized by dry-heat at 180° C. for 2 hours. The pH is adjusted to 7.0. The antibiotic is introduced into the medium after sterilization.

Example 4

Production of L-Lysine by *E. coli* AJ11442 Pl-tacbssR

To test the effect of enhancing expression of the bssR gene on lysine production, the DNA fragments from the chromosome of the above-described *E. coli* strain MG1655 Pl-tacbssR can be transferred to the lysine-producing *E. coli* strain AJ11442 by P1 transduction (Miller, J. H. Experiments in Molecular Genetics, Cold Spring Harbor Lab. Press, 1972, Plainview, N.Y.) to obtain strain AJ11442 Pl-tacbssR. The strain AJ11442 was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM P-5084. Then, it was converted to an international deposit under the provisions of the Budapest Treaty on Oct. 29, 1987, and received an accession number of FERM BP-1543.

Both *E. coli* strains, AJ11442 and AJ11442 Pl-tacbssR, can be cultured in L-medium at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glucose | 40 |
| (NH$_4$)$_2$SO$_4$ | 24 |
| K$_2$HPO$_4$ | 1.0 |
| MgSO$_4$·7H$_2$O | 1.0 |
| FeSO$_4$·7H$_2$O | 0.01 |
| MnSO$_4$·5H$_2$O | 0.01 |
| Yeast extract | 2.0 |

The pH is adjusted to 7.0 by KOH and the medium is autoclaved at 115° C. for 10 min. Glucose and MgSO$_4$.7H$_2$O are sterilized separately. CaCO$_3$ is dry-heat sterilized at 180° C. for 2 hours and added to the medium for a final concentration of 30 g/l.

Example 5

Production of L-Cysteine by *E. coli* Strain JM15(ydeD) Pl-tacbssR

To test the effect of enhancing expression of the bssR gene on L-cysteine production, the DNA fragments from the chromosome of the above-described *E. coli* MG1655 Pl-tacbssR can be transferred to the *E. coli* L-cysteine-producing strain JM15(ydeD) by P1 transduction (Miller, J. H. Experiments in Molecular Genetics, Cold Spring Harbor Lab. Press, 1972, Plainview, N.Y.) to obtain the strain JM15(ydeD) Pl-tacbssR.

*E. coli* strain JM15(ydeD) is a derivative of *E. coli* strain JM15 (U.S. Pat. No. 6,218,168) which can be transformed with DNA having the ydeD gene, which codes for a membrane protein, and is not involved in a biosynthetic pathway of any L-amino acid (U.S. Pat. No. 5,972,663). The strain JM15 (CGSC#5042) can be obtained from The Coli Genetic Stock Collection at the *E. coli* Genetic Resource Center, MCD Biology Department, Yale University (cgsc.biology.yale.edu/).

Fermentation conditions for evaluation of L-cysteine production were described in detail in Example 6 of U.S. Pat. No. 6,218,168.

Example 6

Production of L-Leucine by *E. coli* 57 Pl-tacbssR

To test the effect of enhancing expression of the bssR gene on L-leucine production, the DNA fragments from the chromosome of the above-described *E. coli* strain MG1655 Pl-tacbssR can be transferred to the *E. coli* L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57 Pl-tacbssR. The strain 57 was deposited in the Russian National Collection of Industrial Microorganisms (VKPM) (GNII genetika, 1 Dorozhny proezd, 1, Moscow 117545, Russian Federation) on May 19, 1997 under accession number VKPM B-7386.

Both *E. coli* strains, 57 and 57 Pl-tacbssR, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition:butanol-acetic acid-water=4:1:1).

The composition of the fermentation medium (g/l) (pH 7.2) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 7

Production of L-Histidine by *E. coli* Strain 80 Pl-tacbssr

To test the effect of enhancing expression of the bssR gene on L-histidine production, the DNA fragments from the chromosome of the above-described *E. coli* MG1655 Pl-tacbssR can be transferred to the histidine-producing *E. coli* strain 80 by P1 transduction (Miller, J. H. Experiments in Molecular Genetics, Cold Spring Harbor Lab. Press, 1972, Plainview, N.Y.) to obtain strain 80 Pl-tacbssR. The strain 80 was described in Russian patent 2119536 and deposited in the Russian National Collection of Industrial Microorganisms (GNII genetika, 1 Dorozhny proezd, 1, Moscow 117545, Russian Federation) on Oct. 15, 1999 under accession number VKPM B-7270 and then converted to a deposit under the Budapest Treaty on Jul. 12, 2004.

Both *E. coli* strains, 80 and 80 Pl-tacbssR, can each be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 8

Production of L-Glutamic Acid by *E. coli* Strain VL334thrC+ Pl-tacbssR

To test the effect of enhancing expression of the bssR gene on L-glutamic acid production, the DNA fragments from the chromosome of the above-described *E. coli* strain MG1655 Pl-tacbssR can be transferred to the *E. coli* L-glutamic acid-producing strain VL334thrC+ (EP 1172433) by P1 transduction (Miller, J. H. Experiments in Molecular Genetics, Cold Spring Harbor Lab. Press, 1972, Plainview, N.Y.) to obtain the strain VL334thrC+-Pl-tacbssR. The strain VL334thrC+ was deposited in the Russian National Collection of Industrial Microorganisms (VKPM) (GNII genetika, 1 Dorozhny proezd, 1, Moscow 117545, Russian Federation) on Dec. 6, 2004 under the accession number VKPM B-8961 and then converted to an international deposit under the Budapest Treaty on Dec. 8, 2004.

Both strains, VL334thrC+ and VL334thrC+ Pl-tacbssR, can be grown for 18-24 hours at 37° C. on L-agar plates. Then, one loop of the cells can be transferred into test tubes containing 2 ml of fermentation medium. The fermentation medium contains glucose (60 g/l), ammonium sulfate (25 g/l), KH2PO4 (2 g/l), MgSO4 (1 g/l), thiamine (0.1 mg/ml), L-isoleucine (70 µg/ml), and $CaCO_3$ (25 g/l). The pH is adjusted to 7.2. Glucose and $CaCO_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 9

Production of L-Phenylalanine by *E. coli* Strain AJ12739 Pl-tacbssR

To test the effect of enhancing expression of the bssR gene on L-phenylalanine production, the DNA fragments from the chromosome of the above-described *E. coli* MG1655 Pl-tacbssR can be transferred to the phenylalanine-producing *E. coli* strain AJ12739 by P1 transduction (Miller, J. H. Experiments in Molecular Genetics, Cold Spring Harbor Lab. Press, 1972, Plainview, N.Y.) to obtain strain AJ12739 Pl-tacbssR. The strain AJ12739 was deposited in the Russian National Collection of Industrial Microorganisms (VKPM) (GNII genetika, 1 Dorozhny proezd, 1, Moscow 117545, Russian Federation) on Nov. 6, 2001 under accession no. VKPM B-8197 and then converted to a deposit under the Budapest Treaty on Aug. 23, 2002.

Both strains, AJ12739 and AJ12739 Pl-tacbssR, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:4:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° C. for 2 hours. The pH is adjusted to 7.0.

Example 10

Production of L-Tryptophan by *E. coli* Strain SV164 (pGH5) Pl-tacbssR

To test the effect of enhancing expression of the bssR gene on L-tryptophan production, the DNA fragments from the chromosome of the above-described *E. coli* strain MG1655 Pl-tacbssR can be transferred to the tryptophan-producing *E. coli* strain SV164 (pGH5) by P1 transduction (Miller, J. H. Experiments in Molecular Genetics, Cold Spring Harbor Lab. Press, 1972, Plainview, N.Y.) to obtain the strain SV164 (pGH5) Pl-tacbssR. The strain SV164 was obtained by introducing the trpE allele encoding anthranilate synthase free from feedback inhibition by tryptophan into a trpE deficient strain, *E. coli* KB862 (DSM7196) (WO94/08031, Japanese Patent Laid-open No. 7-507693). The plasmid pGH5 harbors a mutant serA gene encoding phosphoglycerate dehydrogenase free from feedback inhibition by serine. The strain SV164 (pGH5) was described in detail in U.S. Pat. No. 6,180,373 and European patent 0662143. The KB862 strain was designated AJ13828 and was deposited on Dec. 21, 2000 in the National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) as an international deposit under the provisions of the Budapest Treaty with a deposit number of FERM BP-7405.

Both strains, SV164(pGH5) and SV164(pGH5) Pl-tacbssR, can be cultivated with shaking at 32° C. for 18 hours in 3 ml of nutrient broth supplemented with tetracycline (10 mg/ml, marker of pGH5 plasmid). The obtained cultures (0.3 ml each) can be inoculated into 3 ml of a fermentation medium containing tetracycline (10 mg/ml) in 20×200-mm test tubes, and cultivated at 32° C. for 72 hours with a rotary shaker at 250 rpm. After cultivation, the amount of tryptophan which accumulates in the medium can be determined by TLC as described in Example 9.

The fermentation medium components are listed in Table 2, but should be sterilized in separate groups (A, B, C, D, E, F, G and H), as shown, to avoid adverse interactions during sterilization.

TABLE 2

| Solutions | Component | Final concentration, g/l |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | $MgSO_4 \cdot 7H_2O$ | 0.3 |
| C | $CaCl_2$ | 0.011 |
| D | $FeSO_4 \cdot 7H_2O$ | 0.075 |
| | Sodium citrate | 1.0 |
| E | $Na_2MoO_4 \cdot 2H_2O$ | 0.00015 |
| | $H_3BO_3$ | 0.0025 |
| | $CoCl_2 \cdot 6H_2O$ | 0.00007 |
| | $CuSO_4 \cdot 5H_2O$ | 0.00025 |
| | $MnCl_2 \cdot 4H_2O$ | 0.0016 |
| | $ZnSO_4 \cdot 7H_2O$ | 0.0003 |
| F | Thiamine HCl | 0.005 |
| G | $CaCO_3$ | 30.0 |
| H | Pyridoxine | 0.03 |

The pH of solution A is adjusted to 7.1 with $NH_4OH$.

Example 11

Production of L-Proline by *E. coli* Strain 702ilvA Pl-tacbssR

To test the effect of enhancing expression of the bssR gene on L-proline production, the DNA fragments from the chromosome of the above-described *E. coli* strain MG1655 Pl-tacbssR can be transferred to the proline-producing *E. coli* strain 702ilvA by P1 transduction (Miller, J. H. Experiments in Molecular Genetics, Cold Spring Harbor Lab. Press, 1972, Plainview, N.Y.) to obtain strain 702ilvA Pl-tacbssR. The strain 702ilvA was deposited in the Russian National Collection of Industrial Microorganisms (VKPM) (GNII genetika, 1 Dorozhny proezd, 1, Moscow 117545, Russian Federation) on Jul. 18, 2000 under accession number VKPM B-8012 and then converted to an international deposit under the Budapest Treaty on May 18, 2001.

Both E. coli strains, 702ilvA and 702ilvA Pl-tacbssR, can be grown for 18-24 hours at 37° C. on L-agar plates. Then, these strains can be cultivated under the same conditions as in Example 8.

Example 12

Production of L-Citrulline by E. coli Strain 382ΔargG Pl-tacbssR

To test the effect of enhancing expression of the bssR gene on L-citrulline production, the DNA fragments from the chromosome of the above-described E. coli strain MG1655 Pl-tacbssR can be transferred to the E. coli L-citrulline producing strain 382ΔargG by P1 transduction (Miller, J. H. Experiments in Molecular Genetics, Cold Spring Harbor Lab. Press, 1972, Plainview, N.Y.) to obtain the strain 382ΔargG Pl-tacbssR. The strain 382ΔargG can be obtained by deletion of argG gene on the chromosome of 382 strain (VKPM B-7926) by the method initially developed by Datsenko, K. A. and Wanner, B. L. called "Red-driven integration" (Proc. Natl. Acad. Sci. USA, 2000, 97(12), 6640-6645). According to this procedure, the PCR primers homologous to both the region adjacent to the argG gene and the gene which confers antibiotic resistance in the template plasmid can be constructed. The plasmid pMW118-attL-Cm-attR (WO 05/010175) can be used as the template in the PCR reaction.

Both E. coli strains, 382ΔargG and 382ΔargG Pl-tacbssR, can be separately cultivated with shaking at 37° C. for 18 hours in 3 ml of nutrient broth, and 0.3 ml of the obtained cultures were inoculated into 2 ml of a fermentation medium in 20×200-mm test tubes and cultivated at 32° C. for 48 hours on a rotary shaker.

After the cultivation, the amount of citrulline which accumulates in the medium can be determined by paper chromatography using the following mobile phase:butanol:acetic acid:water=4:1:1 (v/v). A solution of ninhydrin (2%) in acetone can be used as a visualizing reagent. A spot containing citrulline can be cut out, citrulline can be eluted with 0.5% water solution of CdCl2, and the amount of citrulline can be estimated spectrophotometrically at 540 nm.

The composition of the fermentation medium (g/l) can be as follows:

| | |
|---|---|
| Glucose | 48.0 |
| $(NH_4)_2SO_4$ | 35.0 |
| $KH_2PO_4$ | 2.0 |
| $MgSO_4·7H_2O$ | 1.0 |
| Thiamine HCl | 0.0002 |
| Yeast extract | 1.0 |
| L-isoleucine | 0.1 |
| L-arginine | 0.1 |
| $CaCO_3$ | 5.0 |

Glucose and magnesium sulfate are sterilized separately. $CaCO_3$ is dry-heat sterilized at 180° C. for 2 hours. The pH is adjusted to 7.0.

Example 13

Production of L-Ornithine by E. coli Strain 382ΔargFΔargI Pl-tacbssR

To test the effect of enhancing expression of the bssR gene on L-ornithine production, the DNA fragments from the chromosome of the above-described E. coli strain MG1655 Pl-tacbssR can be transferred to the E. coli L-ornithine producing strain 382ΔargFΔargI by P1 transduction (Miller, J. H. Experiments in Molecular Genetics, Cold Spring Harbor Lab. Press, 1972, Plainview, N.Y.) to obtain the strain 382ΔargFΔargI Pl-tacbssR. The strain 382 ΔargFΔargI can be obtained by consecutive deletion of argF and argI genes on the chromosome of 382 strain (VKPM B-7926) by the method initially developed by Datsenko, K. A. and Wanner, B. L. called "Red-driven integration" (Proc. Natl. Acad. Sci. USA, 2000, 97(12), 6640-6645). According to this procedure, two pairs of PCR primers homologous to both the region adjacent to the argF or argI gene and the gene which confers antibiotic resistance in the template plasmid can be constructed. The plasmid pMW118-attL-Cm-attR (WO 05/010175) can be used as the template in the PCR reaction.

Both E. coli strains, 382ΔargFΔargI and 382 ΔargFΔargI Pl-tacbssR, can be separately cultivated with shaking at 37° C. for 18 hours in 3 ml of nutrient broth, and 0.3 ml of the obtained cultures were inoculated into 2 ml of a fermentation medium in 20×200-mm test tubes and cultivated at 32° C. for 48 hours on a rotary shaker.

After the cultivation, the amount of ornithine which accumulates in the medium can be determined by paper chromatography using the following mobile phase: butanol:acetic acid:water=4:1:1 (v/v). A solution of ninhydrin (2%) in acetone can be used as a visualizing reagent. A spot containing ornithine can be cut out, ornithine can be eluted with 0.5% water solution of $CdCl_2$, and the amount of ornithine can be estimated spectrophotometrically at 540 nm.

The composition of the fermentation medium (g/l) can be as follows:

| | |
|---|---|
| Glucose | 48.0 |
| $(NH_4)_2SO_4$ | 35.0 |
| $KH_2PO_4$ | 2.0 |
| $MgSO_4·7H_2O$ | 1.0 |
| Thiamine HCl | 0.0002 |
| Yeast extract | 1.0 |
| L-isoleucine | 0.1 |
| L-arginine | 0.1 |
| $CaCO_3$ | 5.0 |

Glucose and magnesium sulfate are sterilized separately. $CaCO_3$ is dry-heat sterilized at 180° C. for 2 hours. The pH is adjusted to 7.0.

Example 14

Production of L-Valine by E. coli Strain H-81 Pl-tacbssR

To test the effect of enhancing expression of the bssR gene on L-valine production, the DNA fragments from the chromosome of the above-described E. coli strain MG1655 Pl-tacbssR can be transferred to the valine-producing E. coli strain H-81 by P1 transduction (Miller, J. H. Experiments in Molecular Genetics, Cold Spring Harbor Lab. Press, 1972, Plainview, N.Y.) to obtain strain H-81 Pl-tacbssR. The H-81 strain was deposited at the Russian National Collection of Industrial Microorganisms (VKPM) (GNII genetika, 1 Dorozhny proezd, 1, Moscow 117545, Russian Federation) on Jan. 30, 2001 under the accession number VKPM B-8066, and it was then converted to an international deposit under the provisions of the Budapest Treaty on Feb. 1, 2002.

The strains H-81 and H-81 Pl-tacbssR can be cultivated at 37° C. for 18 hours in a nutrient broth and 0.1 ml of each of the obtained cultures can be inoculated into 2 ml of fermentation medium in a 20×200 mm test tube and cultivated at 32° C. for 72 hours with a rotary shaker. After cultivation for 48 hours and for 72 hours accumulated amounts of L-valine can be measured by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

Fermentation Medium Composition (g/l):

| | |
|---|---|
| Glucose | 60.0 |
| (NH$_4$)$_2$SO$_4$ | 18.0 |
| KH$_2$PO$_4$ | 1.8 |
| MgSO$_4$·7H$_2$O | 1.2 |
| CaCO$_3$ | 20.0 |
| Thiamine HCl | 0.001 |

CaCO$_3$ is dry-heat sterilized at 180° C. for 2 hours. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of L-amino acid by a bacterium of the Enterobacteriaceae family can be improved.

The invention claimed is:

1. A method for producing an L-amino acid comprising cultivating an L-amino acid-producing bacterium of genus *Escherichia* in a culture medium, and collecting said L-amino acid from the culture medium,
 wherein said bacterium has been modified to enhance the expression of a bssR gene as compared to a non-modified bacterium,
 wherein said bssR gene comprises:
 i) the nucleotide sequence of SEQ ID NO:1, or
 ii) a nucleotide sequence which a) hybridizes with the complete complement of the nucleotide sequence of SEQ ID NO:1 under stringent conditions comprising washing at a salt concentration of 0.1×SSC, 0.1% SDS at 60° C., and b) encodes a protein which has all of the same activities as a protein consisting of the amino acid sequence of SEQ ID NO:2;
 wherein said expression is enhanced by a method selected from the group consisting of:
 a) replacing the native promoter of the bssR gene with a more potent promoter,
 b) increasing the DNA copy number of the bssR gene per cell, and
 c) combinations thereof.

2. The method according to claim 1, wherein said L-amino acid is selected from the group consisting of an aromatic L-amino acid and a non-aromatic L-amino acid.

3. The method according to claim 2, wherein said aromatic L-amino acid is selected from the group consisting of L-phenylalanine, L-tyrosine, and L-tryptophan.

4. The method according to claim 2, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-citrulline, and L-ornithine.

5. The method according to claim 1, wherein said L-amino acid is L-arginine.

* * * * *

SEQUENCE LISTING

```
<160> NUMBER OF SEQ ID NOS: 7

<210> SEQ ID NO 1
<211> LENGTH: 384
<212> TYPE: DNA
<213> ORGANISM: Escherichia coli
<220> FEATURE:
<221> NAME/KEY: CDS
<222> LOCATION: (1)..(384)

<400> SEQUENCE: 1 atg ttc gtt gac aga cag cga atc gat ctg ctg aac cgg ttg atc gac      48
Met Phe Val Asp Arg Gln Arg Ile Asp Leu Leu Asn Arg Leu Ile Asp
1               5                   10                  15 gca cgc gtt gac ctc gcc gca tac gtg caa ctg agg aag gca aaa gga      96
Ala Arg Val Asp Leu Ala Ala Tyr Val Gln Leu Arg Lys Ala Lys Gly
                20                  25                  30 tac atg tcc gtc agc gaa agc aat cat cta cga gat aac ttt ttt aaa     144
Tyr Met Ser Val Ser Glu Ser Asn His Leu Arg Asp Asn Phe Phe Lys
            35                  40                  45 ctg aat cgc gaa ctg cac gat aaa tcg ctg cgg ttg aat ctt cat ctg     192
Leu Asn Arg Glu Leu His Asp Lys Ser Leu Arg Leu Asn Leu His Leu
        50                  55                  60 gat cag gaa gag tgg agt gct ctt cat cat gct gaa gaa gca tta gcg     240
Asp Gln Glu Glu Trp Ser Ala Leu His His Ala Glu Glu Ala Leu Ala
65                  70                  75                  80 aca gcc gca gta tgt ttg atg agt ggg cac cat gat tgc ccg act gtt     288
Thr Ala Ala Val Cys Leu Met Ser Gly His His Asp Cys Pro Thr Val
                85                  90                  95 att acc gtc aac gcc gat aag ctt gaa aat tgt ctg atg agc tta acg     336
Ile Thr Val Asn Ala Asp Lys Leu Glu Asn Cys Leu Met Ser Leu Thr
                100                 105                 110 ctg agt atc cag agc ctg cag aag cac gcc atg ctt gag aag gcc tga     384
Leu Ser Ile Gln Ser Leu Gln Lys His Ala Met Leu Glu Lys Ala
            115                 120                 125

<210> SEQ ID NO 2
<211> LENGTH: 127
<212> TYPE: PRT
<213> ORGANISM: Escherichia coli

<400> SEQUENCE: 2
```

```
Met Phe Val Asp Arg Gln Arg Ile Asp Leu Leu Asn Arg Leu Ile Asp
1               5                   10                  15

Ala Arg Val Asp Leu Ala Ala Tyr Val Gln Leu Arg Lys Ala Lys Gly
            20                  25                  30

Tyr Met Ser Val Ser Glu Ser Asn His Leu Arg Asp Asn Phe Phe Lys
        35                  40                  45

Leu Asn Arg Glu Leu His Asp Lys Ser Leu Arg Leu Asn Leu His Leu
    50                  55                  60

Asp Gln Glu Glu Trp Ser Ala Leu His His Ala Glu Glu Ala Leu Ala
65              70                  75                  80

Thr Ala Ala Val Cys Leu Met Ser Gly His His Asp Cys Pro Thr Val
                85                  90                  95

Ile Thr Val Asn Ala Asp Lys Leu Glu Asn Cys Leu Met Ser Leu Thr
            100                 105                 110

Leu Ser Ile Gln Ser Leu Gln Lys His Ala Met Leu Glu Lys Ala
        115                 120                 125

<210> SEQ ID NO 3
<211> LENGTH: 183
<212> TYPE: DNA
<213> ORGANISM: Artificial Sequence
<220> FEATURE:
<223> OTHER INFORMATION: Promoter

<400> SEQUENCE: 3
ctagatctct cacctaccaa acaatgcccc cctgcaaaaa ataaattcat aaaaaacata    60
cagataacca tctgcggtga taaattatct ctggcggtgt tgacaattaa tcatcggctc   120
gtataatgtg tggaattgtg agcggtttaa cattatcagg agagcattat ggctgttact   180
aat                                                                 183

<210> SEQ ID NO 4
<211> LENGTH: 60
<212> TYPE: DNA
<213> ORGANISM: Artificial Sequence
<220> FEATURE:
<223> OTHER INFORMATION: Primer P1

<400> SEQUENCE: 4
acagagttct ggataaaatt tgtatcgcaa tctcatcgct caagttagta taaaaaagct    60

<210> SEQ ID NO 5
<211> LENGTH: 55
<212> TYPE: DNA
<213> ORGANISM: Artificial Sequence
<220> FEATURE:
<223> OTHER INFORMATION: Primer P2

<400> SEQUENCE: 5
gtctgtcaac gaacatactt cgatcctcct cttccccgct cacaattcca cacat         55

<210> SEQ ID NO 6
<211> LENGTH: 23
<212> TYPE: DNA
<213> ORGANISM: Artificial Sequence
<220> FEATURE:
<223> OTHER INFORMATION: Primer P3

<400> SEQUENCE: 6
ttctacagag ttctggataa aat                                            23

<210> SEQ ID NO 7
```

```
<211> LENGTH: 20
<212> TYPE: DNA
<213> ORGANISM: Artificial Sequence
<220> FEATURE:
<223> OTHER INFORMATION: Primer P4

<400> SEQUENCE: 7
tcctcagttg cacgtatgcg                                              20
```